United States Patent [19]

van der Jagt

[11] Patent Number: Plant 6,465

[45] Date of Patent: Dec. 13, 1988

[54] CHRYSANTHEMUM GOLDEN REFLA

[75] Inventor: Martinus van der Jagt, Ter Aar, Netherlands

[73] Assignee: Chrysanthemum Breeders Association, N.V., Curacao, Netherlands Antilles

[21] Appl. No.: 3,541

[22] Filed: Jan. 15, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst & Oliff

[57] ABSTRACT

A new and distinct cultivar of Chrysanthemum plant named Golden Refla, bearing medium sized yellow blooms with a yellow center and a performance of 17 days.

3 Drawing Sheets

BACKGROUND OF THE NEW PLANT

The new plant of the present invention relates to the Chrysanthemum genus.

ORIGIN AND HISTORY OF THE NEW PLANT

The new plant according to the present invention comprises a new and distinct cultivar of Chrysanthemum plant which is a color mutant of a Chrysanthemum named White Refla. The new cultivar was discovered by Martinus van der Jagt at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a medium sized bloom and yellow color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage of the new cultivar.

DESCRIPTION OF THE NEW PLANT

This new variety of Chrysanthemum is of the botanical classification *Chrysanthemum morifolium,* named Golden Refla. When grown in the vicinity of Ter Aar, Holland, it has a response time of approximately eight and a half weeks. This new variety produces medium sized yellow blooms with a yellow center having a performance of 17 days. This new variety of Chrysanthemum has been found to retain its distinctive characteristics throughout successive propagations and may be planted under conventional greenhouse conditions in Holland between weeks 50–32 (fifty–thirty-two).

The following is a description of the plant and characteristics that distinguish it over related known varieties and its antecedents:

Botanical classification: *Chrysanthemum morifolium.*

Bud:

*Size.*—Medium (cross section: 1.2 cm height: 0.7 cm).

*Form.*—Round and pointed.

*Outside color.*—Yellow orange 22 A.

Bloom:

*Size.*—Medium.

*Fully expanded.*—8 cm.

*Borne.*—Single.

*Stems.*—Strong.

*Form.*—Single (daisy).

*Permanence.*—17 days (at 18°–20° C.).

Color:

*Center of flower (Disk Floret).*—Greyed orange 167 A.

*Base of petals.*—Yellow orange 22 A.

*Inside of petals.*—Yellow orange 22 A.

*Reverse of petals.*—Yellow orange 17 B.

*Outer petals.*—Yellow orange 22 A.

*Tonality from a distance.*—A golden yellow single with upstanding petals.

*Discoloration.*—May discolor to yellow orange 13 C at maturity.

Petals:

*Texture.*—Upperside: Rough. Underside: Rough.

*Number.*—28–32.

*Cross-section.*—Inner petals: convex with 2 keels. Outer petals: flat with 2 keels.

*Arrangement.*—Imbricated.

*Persistence.*—Good (strong petals). Some reflexion at the edge when overbloomed.

*Fragrance.*—Typical Chrysanthemum.

Reproductive organs:

*Stamens.*—Normal for a single.

*Pollen.*—A few appear when blooming.

*Styles.*—Green, yellow, columnar. Length: 7 mm.

*Stigmas.*—Yellow, width: 1 mm.

*Ovaries.*—Enclosed in calyx.

Plant:

*Form.*—Spray mum meant for erect culture, herbaceous crop.

*Growth.*—Vigorous.

*Height.*—Tall, 100–105 cm.

*Peduncle.*—Strong. Near the top: 10 cm. Near the middle: 17 cm. Near the bottom: 20 cm.

*Internodes.*—2½–3 cm.

*Flowering response.*—Eight and a half weeks.

Foliage:

*Color.*—Upperside: Green 131 A. Underside: Greyed green 189 A.

*Size.*—Medium, length: 12 cm, width: 7 cm.

*Quantity.*—36–38.

*Shape.*—Pointed, deeply undulated.

*Texture.*—Upperside: Rough. Underside: Smooth, very hirsute.

*Ribs and veins.*—Well developed, clearly marked. Upperside: Ribs normal; not so much veins. Underside: Ribs more pronounced; veins normal.

*Edge.*—Flat (not crenated) and undulated.

In the description above, color references are made to The "R.H.S. Colour Chart" issued by The Royal Horticultural Society, in association with the Flower Council of Holland, Edition February 1986.

What is claimed:

1. A new and distinct cultivar of Chrysanthemum named Golden Refla, as described and illustrated in the foregoing specification and accompanying drawings.

* * * * *

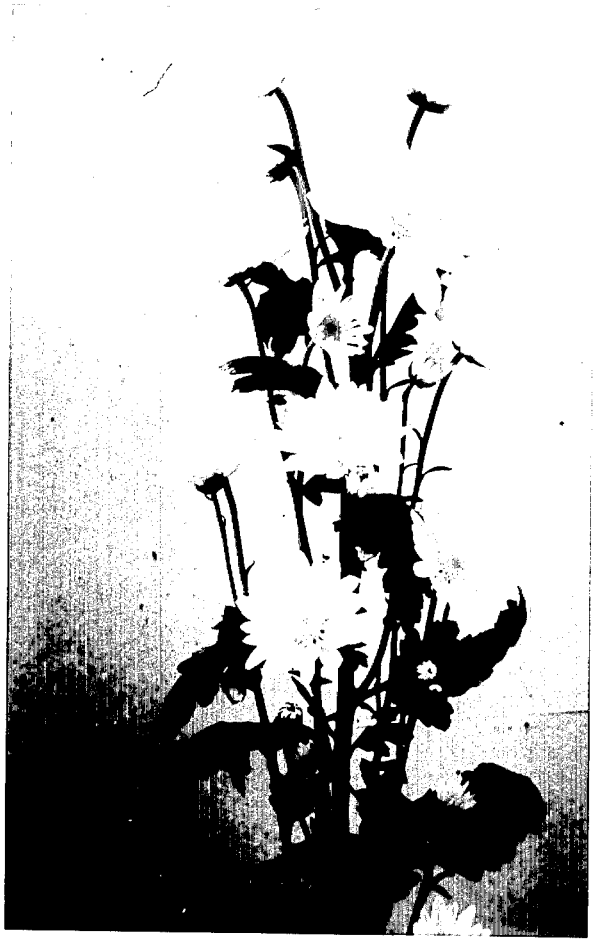

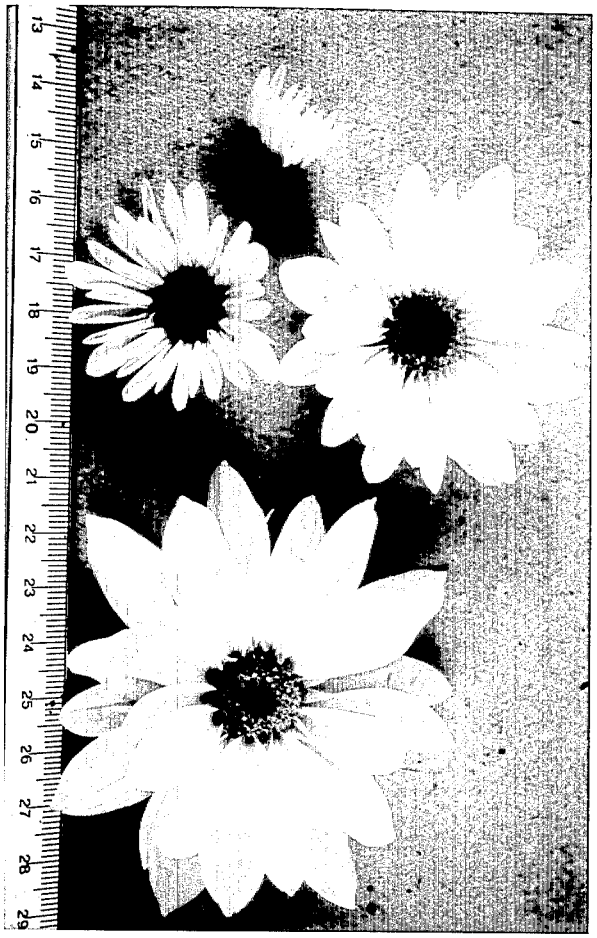
13
14
15
16
17
18
19
20
21
22
23
24
25
26
27
28
29

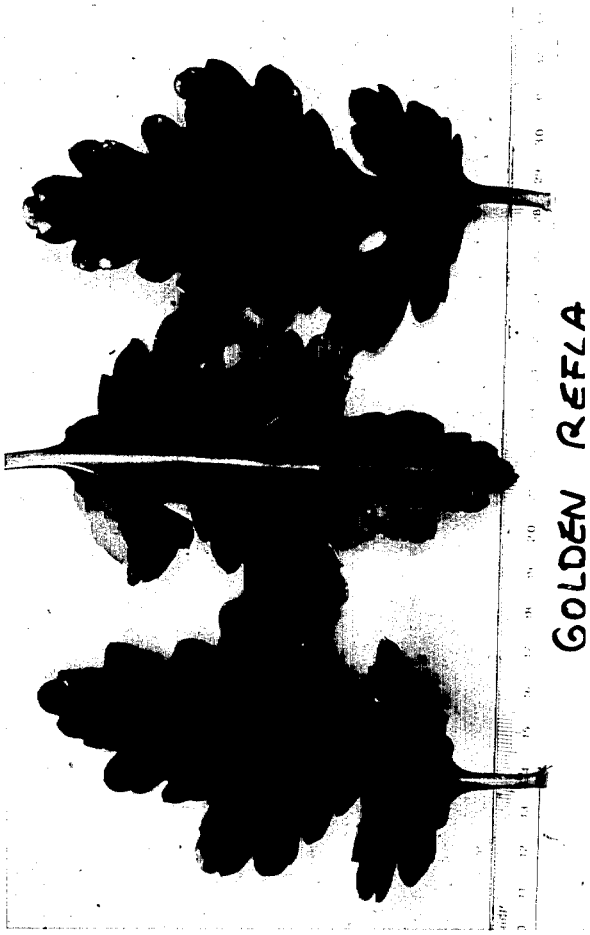
GOLDEN REFLA